United States Patent
Exner et al.

(10) Patent No.: US 7,566,532 B1
(45) Date of Patent: Jul. 28, 2009

(54) METHODS FOR DETECTING RETROVIRUSES

(75) Inventors: Maurice Exner, Mission Viejo, CA (US); Jamie L. Platt, San Juan Capistrano, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 305 days.

(21) Appl. No.: 11/169,287

(22) Filed: Jun. 28, 2005

Related U.S. Application Data

(60) Provisional application No. 60/585,482, filed on Jul. 2, 2004.

(51) Int. Cl.
   C12Q 1/70 (2006.01)
   C12P 19/34 (2006.01)
(52) U.S. Cl. ................ 435/5; 435/91.2; 435/91.32
(58) Field of Classification Search .............. None
   See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis et al. | |
| 5,618,703 A | 4/1997 | Gelfand et al. | |
| 5,876,924 A | 3/1999 | Zhang et al. | |
| 5,962,665 A | 10/1999 | Kroeger et al. | |
| 6,127,115 A | 10/2000 | Ragland et al. | |
| 6,274,320 B1 | 8/2001 | Rothberg et al. | |
| 6,379,191 B1 | 4/2002 | Goetz et al. | |
| 6,495,350 B1 | 12/2002 | Lee et al. | |
| 6,500,620 B2 | 12/2002 | Yu et al. | |
| 6,518,019 B2 | 2/2003 | Gerard et al. | |
| 6,532,276 B1 | 3/2003 | Hartick et al. | |
| 6,569,647 B1 | 5/2003 | Zhang et al. | |
| 6,593,086 B2 | 7/2003 | Zhang et al. | |

OTHER PUBLICATIONS

Treurnicht, et al. Genotypic and phenotypic Analysis of the Env Gene from South African HIV-1 Subtype B and C Isolates. J Med Virol. 2002; 68:141-146.*

Bao, et al. Construction of a cDNA fragment library from SH-SY5Y cells using restriction display PCR. Brit. J Biomed Sci. 2002; 59(1): 35-37.*

Caterino-de-Araujo, et al. HTLV-I/HTLV-II Coinfection in an AIDS Patient from Sao Paulo, Brazil. AIDS Res. Human Retrovir. 2000; 16(8):715-719.*

(Continued)

*Primary Examiner*—Mary E Mosher
*Assistant Examiner*—Stuart W Snyder
(74) *Attorney, Agent, or Firm*—Foley & Lardner LLP

(57) ABSTRACT

Disclosed is a method for detecting human retroviral nucleic acids such as human immunodeficiency virus type I (HIV-1) nucleic acid, human T-cell leukemia virus type I (HTLV-I) nucleic acid, and human T-cell leukemia virus type II (HTLV-II) nucleic acid in a sample. In the method, the sample is treated with reverse transcriptase to generate cDNA, and the cDNA is subsequently analyzed to detect HIV-1, HTLV-I, and HTLV-II. The method may include performing PCR and the method may utilize specific primers. In addition, the method may utilize HTLV linkers that facilitate PCR amplification and sequencing. The cDNA may be treated with restriction enzymes before or after PCR amplification to facilitate sequencing and detection of HIV-1, HTLV-I, or HTLV-II nucleic acid.

15 Claims, 4 Drawing Sheets

OTHER PUBLICATIONS

Meng, et al. Automated Multiplex Assay System for Simultaneous Detection of Hepatitis B Virus DNA, Hepatitis C Virus RNA, and Human Immunodeficiency Virus Type 1 RNA. J Clin Microbiol. 2001; 39(8):2937-2945.*

Fujiwara, et al. PCR with deoxyinosine-containing primers using DNA polymerases with proofreading Activity. PCR Methods and Applications. 1995; 4:239-240.*

Krizman, et al. Construction of a Representative cDNA Library from Prostatic Intfaepithelial Neoplasia. Canc Res. 1996; 56:5380-5383.*

Nagesh, et al., Application of linker-ligation-PCR for construction of phage display epitope libraries. J Virol Meth. 1996; 60:147-154.*

Overmyer, et al. Enrichment of chromosome specific hncDNAs by magnetic bead coupled Alu Sequences. Mol Biol. Rep. 1996; 22:53-57.*

Smith and Roth. Purification and Characterization of an Active Human Immunodeficiency Virus Type 1 RNase H Domain. Journal of Virology. 1993; vol. 67, No. 7:4037-4049.*

Pierson, et al. Molecular Characterization of Preintegration Latency in Human Immunodeficiency Virus Type 1 Infection. Journal of Virology. 2002; vol. 76, No. 17:8518-8531.*

Altschul et al., "Gapped BLAST and PSI-BLAST: a new generation of protein database search programs." Nucl. Acids Res., 25:3389-3402, 1997.

Altschul et al., "Basic Local Alignment Search Tool," J. Mol. Biol., 215:403-410, 1990.

Dolnik, "DNA sequencing by capillary electrophoresis (review)," J Biochem Biophys Methods, 41:103-19, 1999.

Dovichi et al., "DNA Sequencing by Capillary Array Electrophoresis," Methods Mol Biol, 167:225-39, 2001.

Hafner et al., "Isothermal Amplification and Multimerization of DNA by Bst DNA Polymerase," Biotechniques, Apr. 30(4):852-6, 858, 860, 2001.

Heller, "Principles of DNA separation with capillary electrophoresis," Electrophoresis, 22:629-43, 2001.

Karlin and Altschul, "Applications and statistics for multiple high-scoring segments in molecular sequences," Proc. Natl. Acad. Sci. USA, 90:5873, 1993.

Mitchelson, "The Application of Capillary electrophoresis for DNA Polymorphism Analysis," Methods Mol Biol, 162:3-26, 2001.

Needleman and Wunsch, "A General Method Applicable to the Search for Similarities in the Amino Acid Sequence of Two Proteins," J. Mol. Biol., 48:443, 1970.

Pearson and Lipman, Improved tools for biological sequence comparison, Proc. Nat'l. Acad. Sci. USA 85:2444, 1988.

Saiki, "Amplification of Genomic DNA" in PCR Protocols, Innis et al., Eds., Academic Press, San Diego, CA, pp. 13-20, 1990.

Smith and Waterman, "Comparison of Biosequences," Adv. Appl. Math. 2:482, 1981.

Wharam et al., "Specific detection of DNA and RNA targets using a novel isothermal nucleic acid amplification assay based on the formation of a three-way junction structure," Nucleic Acids Res., Jun 1;29(11):E54-E54, 2001.

* cited by examiner

METHODS FOR DETECTING RETROVIRUSES

This application claims priority to U.S. Provisional Patent Application No. 60/585,482 filed Jul. 2, 2004, which is incorporated herein by reference in its entirety, including all tables, figures and claims.

TECHNICAL FIELD

The disclosed method relates to the detection of retroviruses. In particular, the disclosed method relates to the detection of retroviruses such as human immunodeficiency virus and human T-cell leukemia virus. The disclosed method also relates to the primers and/or probes for performing the method.

BACKGROUND

The family Retroviridae comprises a variety of enveloped RNA viruses, such as endogenous retroviruses, leukemia viruses and immunodeficiency viruses, all of which have as their replicative strategy, the essential step of reverse transcription of the virion RNA into linear double-stranded DNA and the subsequent integration of this DNA into the genome of a cell. All retroviruses contain genes for the proteins Gag, Pol, Env, and (often) Pro, while more complex retroviruses, such as HIV-1, contain additional regulatory proteins.

Human immunodeficiency virus 1 (HIV-1) is the causative agent of acquired immunodeficiency syndrome (AIDS). HIV-1 is transmissible in samples of body fluids including blood, plasma, and semen, and as such, it is important to determine whether a sample may be contaminated with HIV-1 before administering the sample in a medical procedure or using the sample to prepare a medical product. For protection of patients who might otherwise receive a sample of HIV-1-infected body fluid, it is particularly important to detect the presence of the virus in the sample to prevent its use in such procedures or in products.

Early-developed tests for detecting HIV-1 relied on detecting anti-HIV-1 antibodies in a sample of body fluid. However, because there is a delay between the time a subject is infected with HIV-1 and the time that the subject develops antibodies against HIV-1, these early-developed tests were prone to false negative results. As such, new tests were developed that could detect HIV-1 nucleic acid in a sample from a subject shortly after the subject has been infected.

Traditional methods for detecting nucleic acids include Southern Blots for detecting DNA, and Northern Blots and RNase mapping for detecting RNA. However, these methods have limited sensitivity. With the advent of reverse transcription ("RT"), the polymerase chain reaction ("PCR"), and automated DNA sequencing, scientists and clinicians were presented with much more sensitive assays for detecting DNA and RNA. For example, methods of performing RT, PCR, reverse transcription followed by PCR ("RT-PCR"), and sequencing are described in U.S. Pat. No. 6,593,086; U.S. Pat. No. 6,569,647; U.S. Pat. No. 6,532,276; U.S. Pat. No. 6,518,019; U.S. Pat. No. 6,500,620; U.S. Pat. No. 6,495,350; U.S. Pat. No. 6,379,191; U.S. Pat. No. 6,274,320; U.S. Pat. No. 6,127,115; U.S. Pat. No. 5,962,665; U.S. Pat. No. 5,876,924; and U.S. Pat. No. 5,618,703.

"Reverse transcriptase" describes a class of polymerases characterized as RNA-dependent DNA polymerases in that they use an RNA template to synthesize a DNA molecule. Historically, reverse transcriptases have been used to reverse-transcribe mRNA into cDNA. However, reverse transcriptases can be used to reverse-transcribe other types of RNAs such as viral genomic RNA or viral sub-genomic RNA. Standard reverse transcriptases include Maloney Murine Leukemia Virus Reverse Transcriptase (MoMuLV RT) and Avian myoblastosis virus (AMV). These enzymes have 5'→3' RNA-dependent DNA polymerase activity, 5'→3' DNA-dependent DNA polymerase activity, and RNase H activity. However, unlike many DNA-dependent DNA polymerases, these enzymes lack 3'→5' exonuclease activity necessary for "proofreading," (i.e., correcting errors made during transcription). After a DNA copy of an RNA has been prepared, the DNA copy may be subjected to various DNA amplification methods such as PCR. Reverse transcription and PCR can be combined in a single assay referred to as RT-PCR.

The PCR process provides a method for amplifying small amounts of DNA, (theoretically a single molecule), into easily detectable amounts. (See U.S. Pat. Nos. 4,683,195 and 4,683,202, which describe the PCR process.) The standard method for PCR requires a template molecule (i.e., the molecule to be amplified), primers that anneal to the template molecule, a DNA dependent DNA polymerase, and a buffer that, in particular, includes nucleotides. The primers are allowed to anneal to the template molecule and the DNA-dependent DNA polymerase extends the primers to create a nascent ds-DNA copy of the template molecule. The sample is then heated to denature the nascent ds-DNA and the primers are again allowed to anneal. As such, the nascent ds-DNA can function as a template molecule for further rounds of ds-DNA synthesis. Because the primers are usually present in excess, the reaction is only limited by the concentration of the template molecule. As the amount of available template increases, the amount of synthesized DNA increases exponentially.

Because the PCR process typically involves heating the sample to denature the ds-DNA, the PCR reaction was not practical until the discovery of thermostable DNA-dependent DNA polymerases. By using a thermostable DNA-dependent DNA polymerase, fresh polymerase need not be added after the sample is heated to denature the dsDNA. The PCR process typically utilizes a DNA polymerase that is stable up to about 93°-95° C.

Reverse transcription and PCR can be used to detect a variety of pathogens including HIV-1. HIV-1 belongs to the family of retroviruses and the subfamily of lentiviruses. Like all retroviruses, HIV-1 is an enveloped, single-stranded (ss), positive-sense (+) RNA virus, and the genome of HIV-1 consists of a dimer of two of the single-stranded RNA molecules. During infection, HIV-1 converts its RNA genome into a DNA copy (i.e., a "provirus") by using its native reverse transcriptase. HIV-1 inserts this DNA copy of its genome into the infected cell's DNA by using a viral enzyme called "integrase." As such, the genome of HIV-1 may be present as an RNA copy or DNA copy within the infected cell.

RT-PCR can be used to detect HIV-1 in blood or tissue samples and to diagnose HIV-1 infection at any time after infection. Diagnosis by RT-PCR is more sensitive and can detect infection earlier than the standard HIV antibody tests (usually an ELISA).

Human T-cell Leukemia Virus types I and II (i.e., HTLV-I and HTLV-II, respectively, also called human T-cell lymphotropic virus types I and II), are members of the family of retroviruses and the subfamily of lentiviruses. HTLV-I has transforming activity in vitro and is etiologically linked to adult T-cell leukemia, which is known to be endemic in several parts of the world. HTLV-II is another retrovirus having transforming capacity in vitro, and has been isolated from a patient with a T-cell variant of hairy cell leukemia. The diagnosis of HTLV-I infection is usually based on serum antibody response to HTLV-I peptide antigens. This usually involves an initial screening assay to identify HTLV-I antibodies, based on an enzyme immunoassay (EIA) with HTLV-I virion peptides. Of those individuals tested for HTLV-I and HTLV-II using standard assays for blood screening, about 0.5-0.05% test positive. However, about 4 out of 5 of the positive results are false positives. Therefore, positive sera is typically tested in a confirmatory assay, such as Western blotting or radioimmunoprecipitation, which detect antibody reactivity with specific HTLV-I peptide antigens.

RT-PCR provides a useful approach for detecting HTLV I and II in peripheral blood mononuclear cells from infected individuals. Early detection of HTLV-I and HTLV-II infection is useful because it is associated with lung pathologies (e.g., increased incidence of pneumonia and acute bronchitis).

As such, improved methods for diagnosing retroviral infections in humans such as those caused by HIV and HTLV is important in treating infected individuals and in controlling the spread of disease.

SUMMARY

Disclosed is a method for detecting in a single assay whether a sample contains an HIV retrovirus and/or an HTLV retrovirus. The method comprises:
a) preparing cDNA by reverse transcribing nucleic acids in the sample;
b) amplifying HIV retrovirus and/or HTLV retrovirus containing nucleic acid using the cDNA as template and a pair of primers specific for HIV and HTLV retroviral nucleic acid;
c) sequencing the amplified nucleic acids; and
d) comparing the sequences with the known nucleotide sequences of HIV and/or HTLV retroviruses to determine if the sample contained an HIV retrovirus and/or an HTLV retrovirus.

cDNA is typically prepared by contacting nucleic acids in or from the sample with a reverse transcriptase mixture which typically includes one or more primers. The primer used for initiating the reverse transcriptase reaction may be a random hexamer or a mixture of random hexamers. The primer may also be a general primer for initiating reverse transcription of a class of RNA molecules (e.g. a poly dT primer for initiating polyadenylated mRNA). Alternatively, the primer may be specific for a retroviral nucleotide sequence such as is present in HIV-1 nucleic acid, HTLV-I nucleic acid, or HTLV-II nucleic acid. After reverse transcription, in one embodiment, cDNA is amplified using primers that specifically anneal to a region of high sequence identity such as sequence shared between HIV-1, HTLV-I, and HTLV-II. In particular, the primers may specifically anneal to a portion of the pol gene of HIV-1, HTLV-I, and HTLV-II, including the protease and/or reverse transcriptase coding sequences. The amplified nucleic acid may then be sequenced using one or more forward or reverse sequencing primers that specifically anneal to the amplified nucleic acid (e.g., at an internal portion of the amplified nucleic acid). The sequences may then be compared with known nucleotide sequences of retroviruses such as HIV-1, HTLV-1 or HTLV-2 to determine the identity of the retroviral nucleic acid present in the sample. Alignment of the sequence results may be helpful to this end. As such, the presence of a retrovirus such as HIV-1, HTLV-I, and/or HTLV-II in the sample may be determined.

In another embodiment, a first oligonucleotide linker is ligated to the cDNA, synthesized as described above, so as to form an anchored-end cDNA. The anchored-end cDNA is then amplified using primers that are specific for the first oligonucleotide linker. The first oligonucleotide linker may include HTLV nucleic acid sequences. After the anchored-end cDNA has been amplified, the amplified cDNA may be fragmented such as by digestion with a restriction enzyme. The fragments may then be ligated to a second oligonucleotide linker to form anchored-end cDNA fragments. The second oligonucleotide linker may be the same as or different than the first oligonucleotide linker. Like the first oligonucleotide linker, the second oligonucleotide linker may include HTLV nucleic acid sequences. After the second oligonucleotide linker has been ligated to the cDNA fragments, the fragments may be sequenced using primers that are specific for the second oligonucleotide linker. The sequences may then be compared with known nucleotide sequences of retroviruses such as HIV-1, HTLV-1 or HTLV-2 to determine the identity of the retroviral nucleic acid present in the sample. Alignment of the sequence results may be helpful to this end.

In another embodiment, the cDNA, synthesized as described above, is treated fragmented such as by digestion with a restriction enzyme, without having been subjected to PCR amplification. The cDNA fragments thus obtained are ligated to an oligonucleotide linker to form anchored-end cDNA fragments. The linker may include HTLV nucleic acid sequences. After the linker has been ligated to the cDNA fragments, the anchored-end cDNA fragments are sequenced using primers that are specific for the oligonucleotide linker. As noted above, the sequences are compared to known sequences to identify the type of retrovirus(es) present in the sample.

In any of the above described embodiments, the method may include isolating and/or enriching the target nucleic acid in a sample prior to reverse transcription. For example, the target nucleic acid may be isolated by capturing the target nucleic acid with an immobilized nucleic acid that anneals to the target nucleic acid during hybridization. In particular, an immobilized nucleic acid (e.g., single-stranded DNA) may be used to capture single stranded nucleic acid (e.g., RNA) corresponding to HIV-1, HTLV-I, and/or HTLV-II prior to performing reverse transcription. The immobilized nucleic acid may be immobilized by a covalent or non-covalent association with a solid support.

As noted above, the oligonucleotide linkers used in the detection method may include HTLV nucleic acid, (e.g., nucleic acid corresponding to HTLV-I or HTLV-II DNA). Further, the oligonucleotide linkers may be of any standard length, typically 10-100 nucleotides, but oligonucleotide linkers of between about 10-40 nucleotides in length are particularly suitable.

Similarly, the primers used for reverse transcription, amplification (e.g. PCR), and/or sequencing may be of any standard length, typically 10-100 nucleotides, but primers of between about 10-40 nucleotides in length are particularly suitable. The primers used in the reverse transcriptase reaction, the amplification, and or sequencing may include standard DNA or RNA nucleotides, (i.e., adenine (A), cytosine (C), thymidine (T), guanine (G), and uracil (U). Alternatively, the primers may include non-standard nucleotides, (i.e., a nucleotide other than A, C, T, G, and U). For example, the primer may comprise inosine, which is a non-specific nucleotide in that it can pair with A, C, T, G, and U. As such, primers that include inosine at a particular nucleotide position have non-specificity at that position. Primers may be designed to anneal to both HIV and HTLV nucleic acids at areas of high percentage identity by incorporating inosine in the primer at nucleotide positions where HIV nucleic acid and HTLV nucleic acid differ. Accordingly, these types of primers may be useful in reverse transcription reactions and/or PCR reactions in which both HIV and/or HTLV nucleic acid may be present as a template molecule.

The primers and/or probes may also incorporate other non-standard nucleotides. For example, nucleotides including modified adenine bases may be incorporated into the primers and/or probes, such as 2,6-amino-1H-purine, which forms three hydrogen bonds with thymidine instead of two.

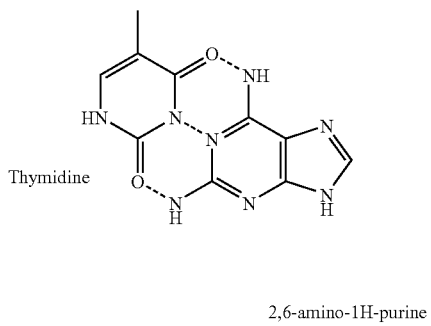

2,6-amino-1H-purine

In addition, a small molecular fragment (R) may be incorporated at the N-7 nitrogen of 2,6-amino-1H-purine and at the C-5 carbon of thymidine, replacing the methyl group. The small molecular fragment R sticks into the major groove of DNA where it is believed to improve base stacking. These molecules are available from Epoch Biosciences under the tradenames Super A™ and Super T™. Super A™ and thymidine are capable of forming three hydrogen bonds with added stability provided by R. Adenine and Super T™ are capable of forming only two hydrogen bonds but with added stability provided by R.

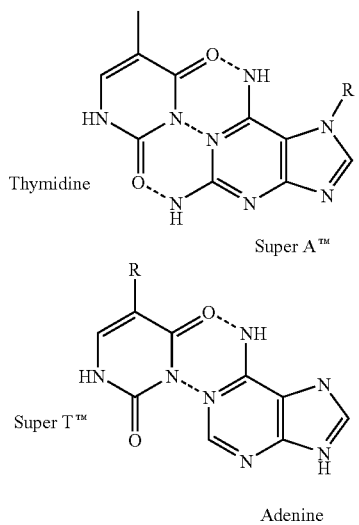

It also may be desirable to incorporate nucleotides that include modified guanine bases into the primers and/or probes. For example, guanine-rich sequences can self-aggregate in solution by forming G-tetrads. G-tetrads are formed partially as the result of hydrogen bonding between the N-7 nitrogen of one guanine base with the hydrogen atoms in the 2-amino group of another guanine base. Bonding as such, four guanine molecules in a four-member daisy chain can form a G-tetrad. To prevent G-tetrad formation and self-aggregation, it may be desirable to incorporate nucleotides that include modified guanine bases into the primers and/or probes, in which the modified guanine base does not include a N-7 nitrogen. One such modified guanine base, Super G™ (Epoch Biosciences), has a nitrogen group at the N-8 position instead of the N-7 position.

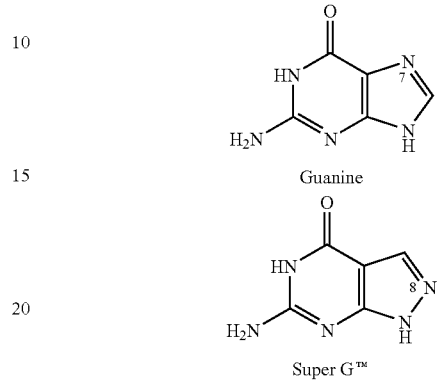

Preferred oligonucleotides of the invention include any of SEQ ID NO: 1 (AAGCICTAITIGAIACAGGAGC); SEQ ID NO: 2 (CCAIIIAATAIICCIGTITTIICIITIAA); SEQ ID NO: 3 (AGATAIIIITIIAIIGTICTICCICAIGGITIIAAA); SEQ ID NO: 4 (ATIIIICAITACATGGATGA); SEQ ID NO: 5 (TII-AIIGTICTICCICAIGGITIIIAAA); SEQ ID NO: 6 (ATAITIIGAGTCTIIIAIIATGTTIA); SEQ ID NO: 7 (CT-TGICCIAITIIATITCICCIA); SEQ ID NO: 8 (TTTIIAIC-CITGIGGIAGIACIITIIAIIIITATCT); or SEQ ID NO: 9 (TTIAIIGIIAAIACIGGIITATTIIITGG). Such oligonucleotides may be substantially purified.

SEQ ID NO: 1 can be used as a forward PCR amplification primer for amplifying from cDNA of HIV-1, HTLV-I or the HTLV-II genome. SEQ ID NOs: 6 and 7, can be used as reverse PCR amplification primers for HIV-1 HTLV-I and the HTLV-II genome.

SEQ ID NOs: 2-5 can be used as a forward sequencing primers for HIV-1 HTLV-I and the HTLV-II genome. SEQ ID NOs: 8 and 9 can be used as a reverse sequencing primers for HIV-1 HTLV-I and the HTLV-II genome.

BRIEF DESCRIPTION OF THE DRAWINGS

FIG. 1A-C is an alignment and comparison of a portion of the pol genes of HIV-1 (SEQ IS NO: 12), HTLV-I (SEQ ID NO: 11), and HTLV-II. (SEQ ID NO: 10), including the protease and reverse transcriptase coding sequences.

DETAILED DESCRIPTION OF THE PREFERRED EMBODIMENTS

Definitions

Figure 2:
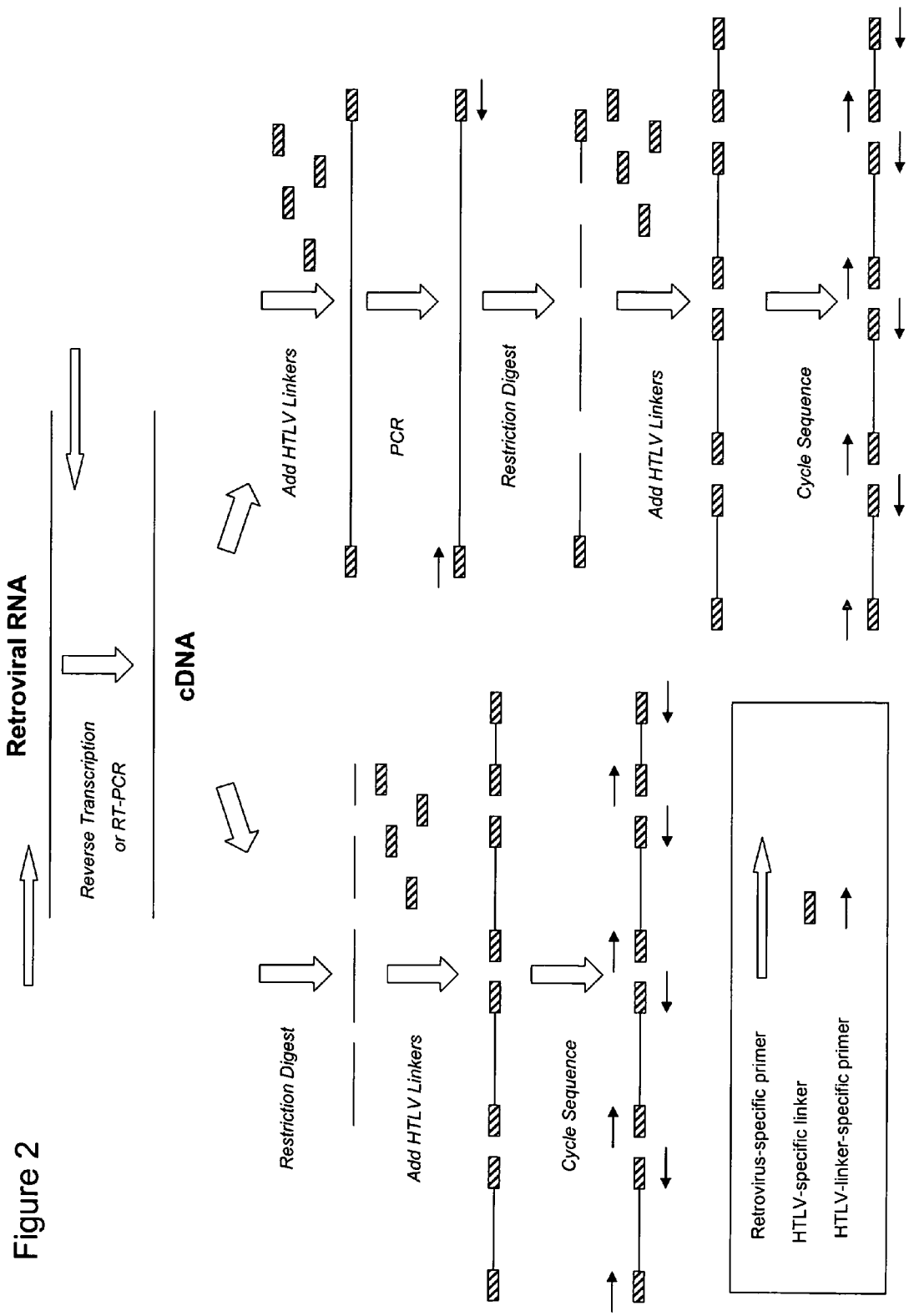
FIG. 2 is a schematic representation of two embodiments of the amplification/detection method.

As used herein, the term "oligonucleotide" refers to a short polymer composed of deoxyribonucleotides, ribonucleotides or any combination thereof. Oligonucleotides of the invention are at least 10 but not more than 100 nucleotides in length. Oligonucleotides are preferably 20 to 70 nucleotides long, with 21 to 26 nucleotides being the most common. The single letter code for nucleotides is as described in the U.S. Patent Office Manual of Patent Examining Procedure, section 2242, table 1. In this regard, the nucleotide designation "R" means guanine or adenine while "Y" means thymine (uracil if RNA) or cytosine.

An oligonucleotide may be used as a primer or as a probe.

As used herein, an "oligonucleotide linker" is a short double-stranded DNA (dsDNA) or single stranded oligonucleotide that is ligated to one or both ends of a DNA molecule. An oligonucleotide-linker is generally from about 12 to about 24 nucleotides in length, although shorter or longer oligonucleotide-linkers may be used. A double-stranded oligonucleotide-linker may be blunt-ended or have sticky ends. A blunt-ended oligonucleotide-linker may be linked to a blunt-ended DNA fragment. Preferable oligonucleotide-linkers have a sticky end that is complementary to a sticky end of a DNA fragment. Oligonucleotide-linkers may be prepared synthetically and, if double-stranded, may be designed with a sticky end by synthesizing top and bottom DNA stands of different length. In another approach, the linker may be synthetically prepared with a blunt end and then treated with an agent to create the appropriate sticky end. For example, a blunt ended oligonucleotide-linker may be treated with the same restriction enzyme used to cleave a piece of DNA to which the linker is to be attached. In this case, a sticky end that is complementary will be generated on both the DNA fragment and the oligonucleotide-linker to be ligated to the fragment.

As used herein, an "anchored-end fragment" is a DNA molecule to which an oligonucleotide linker or linkers have been ligated.

As used herein, an oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity.

As used herein, sequences that have "high sequence identity" have identical nucleotides at least at about 50% of aligned nucleotide positions, preferably at least at about 58% of aligned nucleotide positions, and more preferably at least at about 76% of aligned nucleotide positions.

Sequence identity can be determined using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of identify to various deletions, substitutions and other modifications. The term "identity" in the context of two or more nucleic acids refers to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Methods of alignment of sequence for comparison are well-known in the art. Optimal alignment of sequences for comparison can be conducted, e.g., by the local homology algorithm of Smith and Waterman (1981, Adv. Appl. Math. 2:482) by the homology alignment algorithm of Needleman and Wunsch, (1970, J. Mol. Biol. 48:443) by the search for similarity method of Person and Lipman (1988, Proc. Nat'l. Acad. Sci. USA 85:2444) by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF.

One example of a useful algorithm is BLAST (e.g., BLAST 2.0), which is described in Altschul et al., 1977, *Nucl. Acids Res.* 25:3389-3402, and Altschul et al., J. Mol. Biol., 1990 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra, 1977 and 1990). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment.

The BLASTN program (for nucleotide sequences) uses as defaults a word length (W) of 11, an expectation (E) of 10, M=5, N=−4 and a comparison of both strands. The BLAST algorithm also performs a statistical analysis of the similarity between two sequences (see, e.g., Karlin and Altschul, 1993, Proc. Natl. Acad. Sci. USA 90:5873). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

The length of the amplification primers for use in the present invention depends on several factors including the nucleotide sequence identity and the temperature at which these nucleic acids are hybridized or used during in vitro nucleic acid amplification. The considerations necessary to determine a preferred length for an amplification primer of a particular sequence identity are well known to the person of ordinary skill. For example, the length of a short nucleic acid or oligonucleotide can relate to its hybridization specificity or selectivity.

A primer for reverse transcription and/or amplification such as by PCR is an oligonucleotide that specifically anneals to a target nucleotide sequence. The 3' nucleotide of the primer should be identical to the target sequence at a corresponding nucleotide position.

As used herein, a "general primer" is a primer that may be used to amplify a class of molecules by specifically annealing to a sequence that is common to the class of molecules. For example, a poly dT primer may be used to initiate reverse transcription of the class of RNA molecules called mRNA by binding to the poly A tail present in mRNA.

As used herein, the "pol gene" includes coding sequences for the viral trans-frameshift protein, protease, reverse transcriptase, and integrase. "Coding sequence" means a sequence of nucleotides, either DNA or RNA, which when present in the form of mRNA and translated as amino acids provides at least a portion of a functional protein coded therein.

"Sense strand" means the strand of double-stranded DNA (dsDNA) that includes at least a portion of a coding sequence of a functional protein. "Anti-sense strand" means the strand of dsDNA that is the reverse complement of the sense strand.

As used herein, a "forward primer" is a primer that anneals to the anti-sense strand of dsDNA. A "reverse primer" anneals to the sense-strand of dsDNA.

As used herein, "reverse transcriptase mixture" means any mixture that includes all the components required to synthesize a DNA copy of an RNA molecule. Typically, a "reverse transcriptase mixture" includes reverse transcriptase enzyme and dNTP's in a suitable buffer. A suitable buffer typically includes: (1) a buffering agent such as Tris to maintain a pH of about 8; (2) salt such as KCl; and (3) a source of magnesium ions such as $MgCl_2$. As used herein, the term "hybridize" refers to a process that two complementary nucleic acid strands anneal to each other under appropriately stringent conditions. Hybridizations are typically and preferably conducted with oligonucleotides, preferably 20-100 nucleotides in length. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

The term "stringent hybridization conditions" as used herein refers to hybridization conditions at least as stringent as the following: hybridization in 50% formamide, 5×SSC, 50 mM NaH2PO4, pH 6.8, 0.5% SDS, 0.1 mg/mL sonicated salmon sperm DNA, and 5×Denhardt's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

The term "amplify" with respect to nucleic acid sequences refers to methods that increase the representation of a population of nucleic acid sequences in a sample. Nucleic acid amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(11):E54-E54; Hafner et al., Biotechniques 2001 April; 30(4):852-6, 858, 860; and Zhong et al., Biotechniques 2001 April; 30(4):852-6, 858, 860.

As used herein, the term "sample" refers to any liquid or solid material believed to comprise retroviral nucleic acids. In preferred embodiments, a sample is obtained from a biological source, such as cells in culture or a tissue sample or body fluid from an animal, most preferably, a human. Preferred sample tissues or body fluids include, but are not limited to, plasma, serum, whole blood, blood cells, lymphatic fluid, cerebrospinal fluid, synovial fluid, urine, saliva, and skin or other organs (e.g. biopsy material). The term "patient sample" as used herein refers to a sample obtained from a human seeking diagnosis or treatment for retroviral infection.

As used herein, the term "substantially purified" in reference to oligonucleotides does not require absolute purity. Instead, it represents an indication that the oligonucleotide is relatively more pure than it would be if found in the natural environment. Such oligonucleotides may be obtained by a number of methods including, for example, laboratory synthesis, restriction enzyme digestion or PCR. A "substantially purified" oligonucleotide is preferably greater than 50% pure, more preferably at least 75% pure, and most preferably at least 95% pure.

EXAMPLES

A. Samples. The method may be performed using any biological sample. Biological samples may be obtained by standard procedures and may be used immediately or stored (e.g., the sample may be frozen at about −20° C. to about −70° C.) for later use Samples may be subjected to known methods to facilitate isolation and/or detection of nucleic acids corresponding to HIV-1, HTLV-I, and HTLV-II. For example, the sample may be treated to pellet any virus present in the sample. In addition, any virus or whole cells in the sample may be lysed by conventional means to release any associated nucleic acid. Similarly, a tissue sample may be treated so as to disrupt the tissue structure and/or lyse any whole cells in the sample. Viruses and/or cells may be lysed by treatment with chaotropic agents (e.g., 4 M guanidinium thiocyanate) and/or detergents (e.g., 1% sodium dodecyl sulfate). Samples may be heated to lyse viruses/cells and facilitate release of nucleic acid. An exemplary lysis buffer may include 4 M guanidinium thiocyanate, 25 mM sodium citrate, 0.5% sodium lauroyl sarcosine, 100 mM dithiothreitol, and 80 µg/ml glycogen. Samples may also be treated with proteinase to digest any protein in the sample (e.g., 500 µg/ml proteinase K). In addition, samples may be extracted with organic solvents to remove proteins and/or lipids. For example, samples may be extracted with phenol/chloroform. To precipitate nucleic acid from the sample, ethanol or isopropanol may be added to the sample (e.g., 3 volumes 100% ethanol). The precipitated nucleic acid may be washed (e.g., 3 times with 70% ethanol) to remove any residual salts. The purified nucleic acids may then be dried and resuspended in a suitable buffer (e.g., 10 mM Tris, 1 mM EDTA, pH 7.4).

B. Reverse transcription. The purified nucleic acids may be subjected to a standard reverse transcription reaction. A standard reaction mixture may include: purified nucleic acids; primer (e.g., poly T, random hexamers, or a primer specific for HIV-1, HTLV-I, and HTLV-II at 6.25 µM); nucleotides (dATP, dCTP, dGTP, and dTTP, all at 2.5 mM); and 1-5 U reverse transcriptase (e.g., Maloney Murine Leukemia Virus reverse transcriptase (Perkin Elmer); in a buffer including 25 mM Tris, 50 mM KCl, 6.25 mM $MgCl_2$, pH 8.2 (20 µl total reaction volume). The reaction may be incubated at about 42° C. for about 1 hour. The nucleic acids, including any synthesized cDNA, may be purified (e.g., by extraction with organic solvents and ethanol precipitation) and/or subjected to PCR.

C. Amplification. The reverse transcribed nucleic acids (i.e., cDNA) may be subjected to nucleic acid amplification such as by a standard PCR protocol. A standard reaction mixture may include: cDNA, ~0.5 mM of a forward primer (10-40 nucleotides in length) and a reverse primer (10-40 nucleotides in length); 0.1 mM dATP, dCTP, dGTP, and dTTP; 1-5 U Taq polymerase; in a buffer including 10 mM Tris, 50 mM KCl, 250 mM $MgCl_2$, pH 8.2 (50 µl total reaction volume). The reaction may be performed in a standard thermal cycler (e.g., a Perkin Elmer model 9600, 9700, or 2400). A standard cycle may include:
  (a) one cycle of 95° C. for about 10 minutes;
  (b) 20 cycles of
    (i) 95° C. for 30 seconds;
    (ii) annealing temperature of the primer minus 5° C. for 30 seconds, and
    (iii) 72° C. for 2 minute;
  (c) one cycle of 72° C. for 10 minutes; followed by
  (d) an extended cycle at 4° C.

The annealing temperature of a primer may be calculated by using the "Nearest Neighbor Thermodynamic Formula": $T_m primer = \Delta H [\Delta S + R \ln(c/4)] - 273.15° C. + 16.6 \log_{10}[K+]$. Alternatively, the annealing temperature of a primer may be calculated by using the formula: $T_m = 2(A+T) + 4(G+C)$.

D. Ligation. Linkers may be ligated to the cDNA products using standard protocols. A ligation mixture may include: cDNA; linkers in molar excess (at least about 3-fold); 1-5 U T4 DNA Ligase; in a buffer including 100 mM Tris-HCl pH 7.6, 5 mM $MgCl_2$ 10 mM DTT, 1 mM ATP, (20 µl total reaction volume). The reaction is incubated for about 30 minutes at room temperature.

Linkers of generally from 8 to 20 nucleotides in length may be used, although longer sequences are possible. Virtually any linker sequence may be used that can be targeted by a primer. In a preferred embodiment, the oligonucleotide linker comprises HTLV nucleic acid sequence.

E. Retroviral Specific Primers. Specific primers for amplifying and/or detecting (e.g., sequencing) retroviral nucleic acids such as from HIV-1, HTLV-I and HTLV-II may be selected by comparing the nucleotide sequences of the respective viruses. The primer is selected to correspond to a region of high identity between the compared sequences, preferably a region with at least about 58% identity between the compared sequences, and more preferably a region with at least about 76% identity between the compared sequences. At those positions where the sequences differ, inosine may be used as a non-specific nucleotide.

Figure 1A:
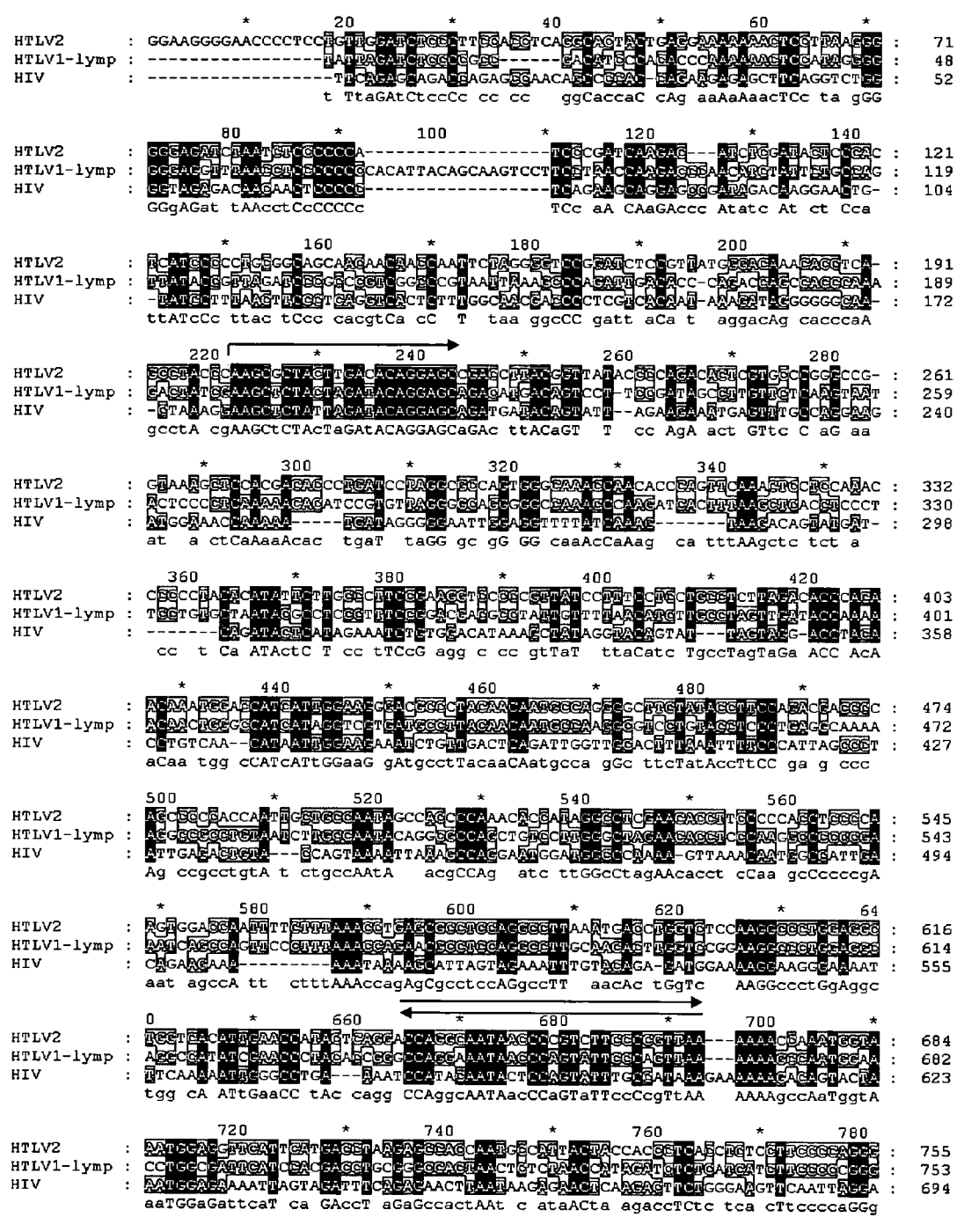
Figure 1B:
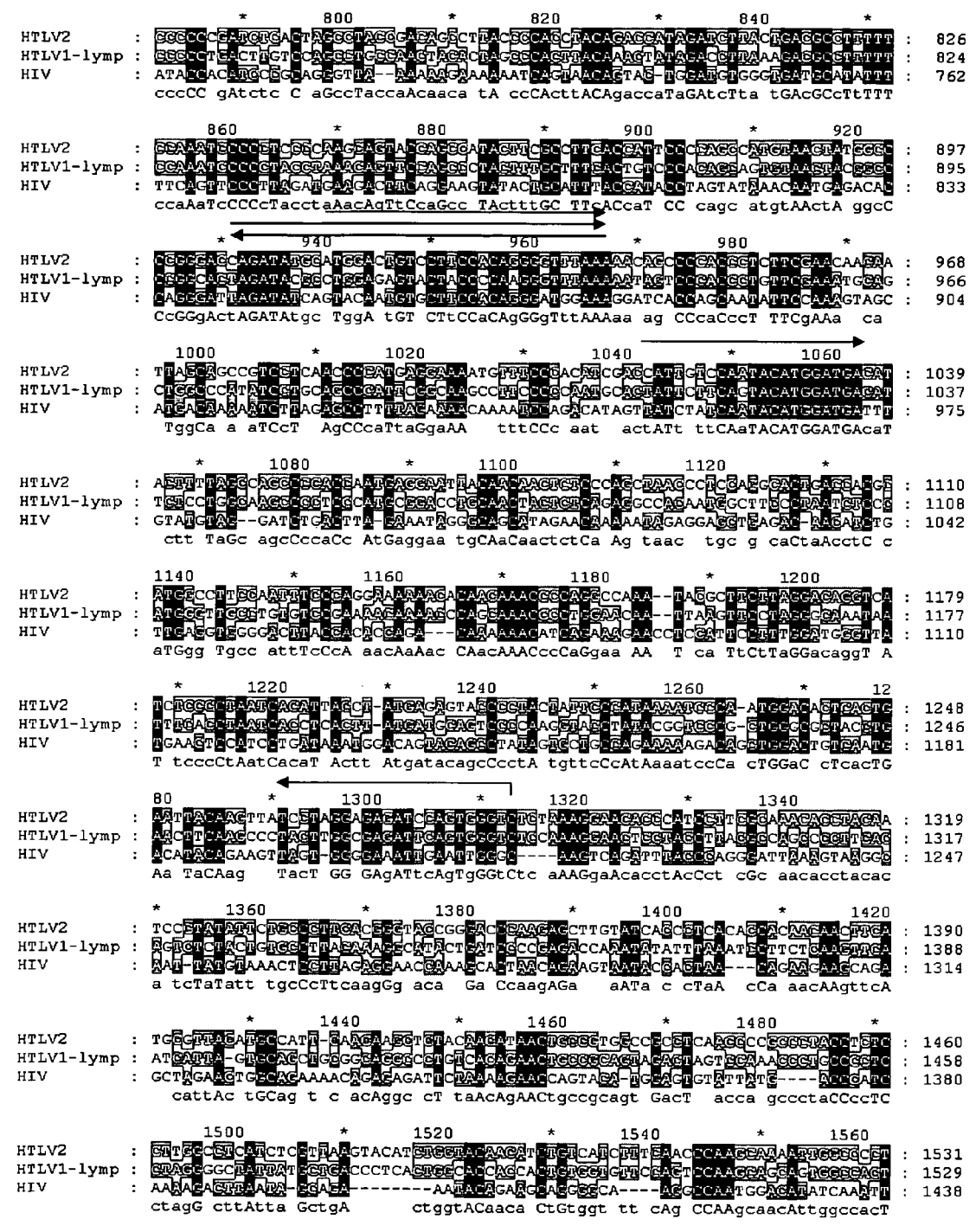
Figure 1C:
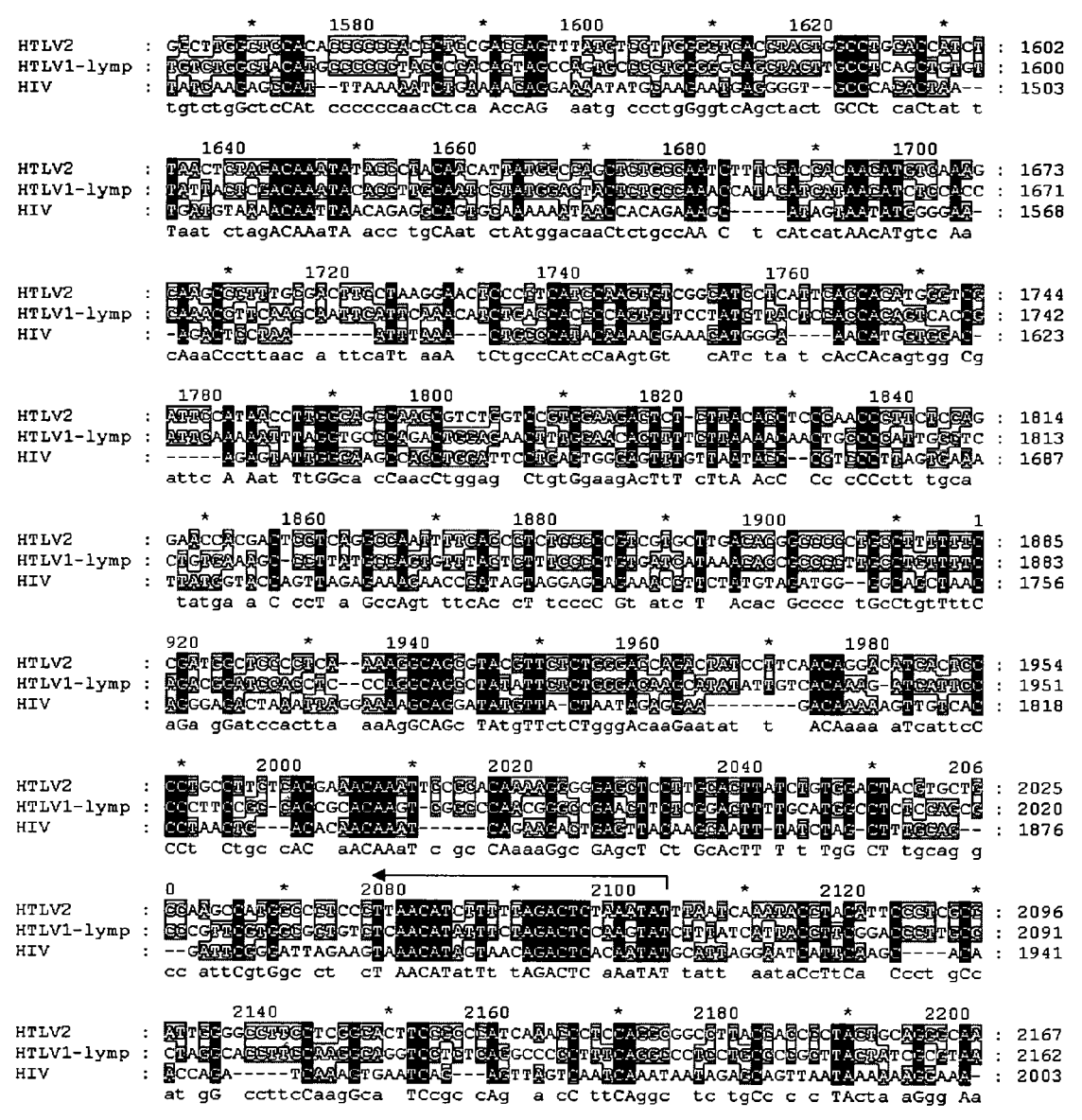

FIG. 1A-C is a sequence alignment of a portion of the pol gene of HIV-1, HTLV-I, and HTLV-II, including the coding sequences for the protease and reverse transcriptase. Based on the alignment of these coding sequences, primers were selected that correspond to regions of high identity. (See forward and reverse arrows as provided above the coding sequence). Exemplary oligonucleotides that may be used as primers include the following primers listed below. Although specifically designated as "PCR Primer" and/or "Sequencing Primer," these oligonucleotides may be used as primers for reverse transcription, PCR, and/or sequencing reactions as appropriate. In the listed sequences, "I" indicates "inosine":

1. Forward PCR Primer

SEQ ID NO: 1 (AAGCICTAITIGAIACAGGAGC) anneals at about nucleotide positions 1860-1881 of the HIV-1 genome, at about nucleotide positions 2240-2261 of the HTLV-I genome, and at about nucleotide positions 2226-2247 of the HTLV-II genome.

2. Forward Sequencing Primer 1

SEQ ID NO: 2 (CCAIIIAATAIICCIGTITTIICIITIAA) anneals at about nucleotide positions 2258-2286 of the HIV-1 genome, at about nucleotide positions 2674-2702 of the HTLV-I genome, and at about nucleotide positions 2668-2696 of the HTLV-II genome.

3. Forward Sequencing Primer 2

SEQ ID NO: 3 (AGATAIIITTIIAIIGTICTICCICAIG-GITIIAAA) anneals at about nucleotide positions 2522-2557 of the HIV-1 genome, at about nucleotide positions 2938-2973 of the HTLV-I genome, and at about nucleotide positions 2932-2967 of the HTLV-II genome.

4. Forward Sequencing Primer 3

SEQ ID NO: 4 (ATIIIICAITACATGGATGA) anneals at about nucleotide positions 2633-2652 of the HIV-1 genome, at about nucleotide positions 3049-3068 of the HTLV-I genome, and at about nucleotide positions 3043-3063 of the HTLV-II genome.

5. Forward Sequencing Primer 4

SEQ ID NO: 5 (TIIAIIGTICTICCICAIGGITIIIAAA) anneals at about nucleotide positions 2531-2557 of the HIV-1 genome, at about nucleotide positions 2947-2973 of the HTLV-I genome, and at about positions 2941-2967 of the HTLV-II genome.

6. Reverse PCR Primer 1

SEQ ID NO: 6 (ATAITIIGAGTCTIIIAIIATGTTIA) anneals at about nucleotide positions 3598-3571 of the HIV-1 genome, at about nucleotide positions 4098-4072 of the HTLV-I genome, and at about nucleotide positions 4095-4069 of the HTLV-II genome.

7. Reverse PCR Primer 2

SEQ ID NO: 7 (CTTGICCIAITIIATITCICCIA) anneals at about nucleotide positions 2992-2877 of the HIV-1 genome), at about nucleotide positions 3316-3296 of the HTLV-I genome, and at about nucleotide positions 3310-3289 of the HTLV-II genome.

8. Reverse Sequencing Primer 2

SEQ ID NO: 8 (TTTIIAICCITGIGGIAGIACIITII-AIIIITATCT) anneals at about nucleotide positions 2557-2522 of the HIV-1 genome, at about nucleotide positions 2973-2938 of the HTLV-I genome, and at about nucleotide positions 2967-2932 of the HTLV-II genome.

9. Reverse Sequencing Primer 1

SEQ ID NO: 9 (TTIAIIGIIAAIACIGGIITATTIIITGG) anneals at about nucleotide position 2286-2258 of the HIV-1 genome, at about nucleotide positions 2702-2674 of the HTLV-I genome, and at about nucleotide positions 2696-2668 of the HTLV-II genome.

F. Sequencing reactions. The amplified cDNA may be sequenced by standard protocols. For example, the amplified cDNA may be further amplified and sequenced using a dye termination protocol. A dye termination protocol includes dye-labeled termination nucleotides (e.g., dideoxy nucleotides), or unlabeled termination nucleotides together with dye-labeled primers. In the first type of reaction using dye-labeled termination nucleotides, fluorescent dye-labeled dideoxy nucleotides are incorporated into a sequence during the extension phase, which may be the extension phase of a PCR cycle. When a dye-labeled dideoxy nucleotide is introduced into the sequence during this phase of the reaction, the extension of the DNA product stops. Termination occurs because the dye-labeled termination nucleotide lacks a 3' hydroxyl group and is incapable of being extended. This type of sequencing reaction will produce a number of different size fragments all containing a dye-labeled dideoxy nucleotide at the end of the fragment. The number of different size fragments will be equal to the number of bases in the sequence. This type of reaction uses four different fluorescent dyes used in cycle sequencing, each one associated with a specific nucleotide (i.e., A, C, G, and T). As such, the sequencing reaction may be performed in a single tube. The products can be visualized and identified by migration through a gel (e.g., by performing PAGE) followed by analysis using an apparatus that incorporates a scanning excitation laser. As the excitation laser scans along the electrophoretic axis of the gel, it excites and detects the emission from each dye (i.e., tag) at each cycle sequencing termination point within the gel.

Fluorescent dye labeled primers may also be used. However, identical primers that are distinctly labeled with four separate dyes, corresponding to A, C, G, and T, must be used in this case. After the sequencing reaction is complete, the different primer reactions may be combined and run as one sample, as long as each reaction used the same primer, (albeit distinctly labeled with a dye corresponding to A, C, G, or T). The above sequencing methods may be conducted by cycling or non-cycling methods.

High throughput sequencing may be used and is preferably conducted using an automated capillary electrophoresis (CE) system, which separates labeled DNA molecules in a size-dependent manner, so that signals corresponding to each nucleotide in a sequence are detected in a sequential fashion. For reviews of the use of CE in DNA sequencing and polymorphism analysis, see Heller, Electrophoresis 22:629-43, 2001; Dovichi et al., Methods Mol Biol 167:225-39, 2001; Mitchelson, Methods Mol Biol 162:3-26, 2001; and Dolnik, J Biochem Biophys Methods 41:103-19, 1999. An ABI PRISM® 3100 Genetic Analyzer used with an ABI PRISM 3100 capillary array, 36-cm (P/N#4315931) provides one useful commercial high throughput sequencing instrument using multi-color fluorescence and 16 capillaries operating in parallel. The MegaBACE™ 1000 DNA Analysis System (Molecular Dynamics, Inc and Amersham Pharmacia Biotech) and the 3700, or 3730-DNA Analyzers (Applied Biosystems) provide 96 capillary CE sequencers.

All references, patents, and/or applications cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compounds/compositions described herein as presently representative of preferred embodiments are exemplary and are not intended as limitations on the scope of the invention. Changes therein and other uses will occur to those skilled in the art, which are encompassed within the invention.

It will be readily apparent to one skilled in the art that varying substitutions and modifications may be made to the invention disclosed herein without departing from the scope and spirit of the invention. Thus, such additional embodiments are within the scope of the present invention.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member or subgroup of members of the Markush group or other group.

The invention claimed is:

1. A method for detecting in a single assay whether a sample contains an HIV retrovirus and/or an HTLV retrovirus, the method comprising:
   a) preparing cDNA by reverse transcribing nucleic acids in the sample;
   b) ligating a first oligonucleotide linker to the cDNA to form an anchored-end cDNA;
   c) amplifying the anchored-end cDNA to form amplified cDNA using primers that specifically anneal to the first oligonucleotide linker;
   d) treating the amplified cDNA with a restriction enzyme to generate cDNA fragments;
   e) ligating a second oligonucleotide linker to the cDNA fragments to form anchored-end cDNA fragments;
   f) sequencing the anchored-end cDNA fragments using sequencing primers that specifically anneal to the second oligonucleotide linker; and
   g) comparing the sequences with the known nucleotide sequences of HIV and/or HTLV retroviruses to determine if the sample contained an HIV retrovirus and/or an HTLV retrovirus.

2. The method of claim 1, wherein the HIV retrovirus is HIV-1.

3. The method of claim 1, wherein the HTLV retrovirus is HTLV-I.

4. The method of claim 1, wherein the HTLV retrovirus is HTLV-II.

5. The method of claim 1, wherein the second oligonucleotide linker comprises HTLV nucleic acid.

6. The method of claim 1, further comprising contacting the sample with an immobilized nucleic acid to capture the HIV retrovirus and/or an HTLV retrovirus nucleic acid in the sample prior to step a).

7. The method of claim 6, wherein the immobilized nucleic acid specifically anneals to at least a portion of the pol gene of HIV-1, HTLV-I, and HTLV-II.

8. The method of claim 1, wherein the first oligonucleotide linker comprises HTLV nucleic acid.

9. The method of claim 1, wherein one or more primers for reverse transcribing, and primers for amplifying and sequencing and the linkers are about 10 to about 100 nucleotides in length.

10. The method of claim 1, wherein one or more primers for reverse transcribing, and primers for amplifying and sequencing and the linkers are about 10 to about 40 nucleotides in length.

11. The method of claim 1, wherein one or more primers for reverse transcribing are specific for HIV-1 nucleic acid, HTLV-I nucleic acid, and HTLV-II nucleic acid.

12. The method of claim 1, wherein one or more primers for reverse transcribing, and primers for amplifying and sequencing comprise a nucleotide other than adenine (A), cytosine (C), thymidine (T), or guanine (G).

13. The method of claim 12, wherein one or more primers for reverse transcribing, and primers for amplifying and sequencing comprise inosine.

14. The method of claim 1, wherein the first oligonucleotide linker and the second oligonucleotide linker are the same.

15. The method of claim 1, wherein the first oligonucleotide linker and the second oligonucleotide linker are different.

* * * * *

SEQUENCE LISTING

<160> NUMBER OF SEQ ID NOS: 12

<210> SEQ ID NO 1
<211> LENGTH: 22
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: inosine
<220> FEATURE:
<221> NAME/KEY: modified_base
<222> LOCATION: (9)..(9)
<223> OTHER INFORMATION: inosine
<220> FEATURE:
<221> NAME/KEY: modified_base
<222> LOCATION: (11)..(11)
<223> OTHER INFORMATION: inosine
<220> FEATURE:
<221> NAME/KEY: modified_base
<222> LOCATION: (14)..(14)
<223> OTHER INFORMATION: inosine

<400> SEQUENCE: 1
aagcnctant nganacagga gc                                                  22

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(6)
<223> OTHER INFORMATION: inosine
<220> FEATURE:
<221> NAME/KEY: modified_base
<222> LOCATION: (11)..(12)
<223> OTHER INFORMATION: inosine
<220> FEATURE:
<221> NAME/KEY: modified_base
<222> LOCATION: (15)..(15)
<223> OTHER INFORMATION: inosine
<220> FEATURE:
<221> NAME/KEY: modified_base
<222> LOCATION: (18)..(18)
<223> OTHER INFORMATION: inosine
<220> FEATURE:
<221> NAME/KEY: modified_base
<222> LOCATION: (21)..(22)
<223> OTHER INFORMATION: inosine
<220> FEATURE:
<221> NAME/KEY: modified_base
<222> LOCATION: (24)..(25)
<223> OTHER INFORMATION: inosine
<220> FEATURE:
<221> NAME/KEY: modified_base
<222> LOCATION: (27)..(27)
<223> OTHER INFORMATION: inosine

<400> SEQUENCE: 2
ccannnaata nnccngtntt nncnntnaa                                           29

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(9)
<223> OTHER INFORMATION: inosine
<220> FEATURE:
```

```
<221> NAME/KEY: modified_base
<222> LOCATION: (11)..(12)
<223> OTHER INFORMATION: inosine
<220> FEATURE:
<221> NAME/KEY: modified_base
<222> LOCATION: (14)..(15)
<223> OTHER INFORMATION: inosine
<220> FEATURE:
<221> NAME/KEY: modified_base
<222> LOCATION: (18)..(18)
<223> OTHER INFORMATION: inosine
<220> FEATURE:
<221> NAME/KEY: modified_base
<222> LOCATION: (21)..(21)
<223> OTHER INFORMATION: inosine
<220> FEATURE:
<221> NAME/KEY: modified_base
<222> LOCATION: (24)..(24)
<223> OTHER INFORMATION: inosine
<220> FEATURE:
<221> NAME/KEY: modified_base
<222> LOCATION: (27)..(27)
<223> OTHER INFORMATION: inosine
<220> FEATURE:
<221> NAME/KEY: modified_base
<222> LOCATION: (30)..(30)
<223> OTHER INFORMATION: inosine
<220> FEATURE:
<221> NAME/KEY: modified_base
<222> LOCATION: (32)..(33)
<223> OTHER INFORMATION: inosine

<400> SEQUENCE: 3
agatannnnt nnanngtnct nccncanggn tnnaaa                              36

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(6)
<223> OTHER INFORMATION: inosine
<220> FEATURE:
<221> NAME/KEY: modified_base
<222> LOCATION: (9)..(9)
<223> OTHER INFORMATION: inosine

<400> SEQUENCE: 4
atnnnncant acatggatga                                                20

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(3)
<223> OTHER INFORMATION: inosine
<220> FEATURE:
<221> NAME/KEY: modified_base
<222> LOCATION: (5)..(6)
<223> OTHER INFORMATION: inosine
<220> FEATURE:
<221> NAME/KEY: modified_base
<222> LOCATION: (9)..(9)
<223> OTHER INFORMATION: inosine
<220> FEATURE:
<221> NAME/KEY: modified_base
```

```
<222> LOCATION: (12)..(12)
<223> OTHER INFORMATION: inosine
<220> FEATURE:
<221> NAME/KEY: modified_base
<222> LOCATION: (15)..(15)
<223> OTHER INFORMATION: inosine
<220> FEATURE:
<221> NAME/KEY: modified_base
<222> LOCATION: (18)..(18)
<223> OTHER INFORMATION: inosine
<220> FEATURE:
<221> NAME/KEY: modified_base
<222> LOCATION: (21)..(21)
<223> OTHER INFORMATION: inosine
<220> FEATURE:
<221> NAME/KEY: modified_base
<222> LOCATION: (23)..(25)
<223> OTHER INFORMATION: inosine

<400> SEQUENCE: 5
tnnanngtnc tnccncangg ntnnnaaa                                            28

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: inosine
<220> FEATURE:
<221> NAME/KEY: modified_base
<222> LOCATION: (6)..(7)
<223> OTHER INFORMATION: inosine
<220> FEATURE:
<221> NAME/KEY: modified_base
<222> LOCATION: (14)..(16)
<223> OTHER INFORMATION: inosine
<220> FEATURE:
<221> NAME/KEY: modified_base
<222> LOCATION: (18)..(19)
<223> OTHER INFORMATION: inosine
<220> FEATURE:
<221> NAME/KEY: modified_base
<222> LOCATION: (25)..(25)
<223> OTHER INFORMATION: inosine

<400> SEQUENCE: 6
atantnngag tctnnnanna tgttna                                              26

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(5)
<223> OTHER INFORMATION: inosine
<220> FEATURE:
<221> NAME/KEY: modified_base
<222> LOCATION: (8)..(8)
<223> OTHER INFORMATION: inosine
<220> FEATURE:
<221> NAME/KEY: modified_base
<222> LOCATION: (10)..(10)
<223> OTHER INFORMATION: inosine
<220> FEATURE:
<221> NAME/KEY: modified_base
<222> LOCATION: (12)..(13)
```

<223> OTHER INFORMATION: inosine
<220> FEATURE:
<221> NAME/KEY: modified_base
<222> LOCATION: (16)..(16)
<223> OTHER INFORMATION: inosine
<220> FEATURE:
<221> NAME/KEY: modified_base
<222> LOCATION: (19)..(19)
<223> OTHER INFORMATION: inosine
<220> FEATURE:
<221> NAME/KEY: modified_base
<222> LOCATION: (22)..(22)
<223> OTHER INFORMATION: inosine

<400> SEQUENCE: 7
cttgnccnan tnnatntcnc cna                                          23

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(5)
<223> OTHER INFORMATION: inosine
<220> FEATURE:
<221> NAME/KEY: modified_base
<222> LOCATION: (7)..(7)
<223> OTHER INFORMATION: inosine
<220> FEATURE:
<221> NAME/KEY: modified_base
<222> LOCATION: (10)..(10)
<223> OTHER INFORMATION: inosine
<220> FEATURE:
<221> NAME/KEY: modified_base
<222> LOCATION: (13)..(13)
<223> OTHER INFORMATION: inosine
<220> FEATURE:
<221> NAME/KEY: modified_base
<222> LOCATION: (16)..(16)
<223> OTHER INFORMATION: inosine
<220> FEATURE:
<221> NAME/KEY: modified_base
<222> LOCATION: (19)..(19)
<223> OTHER INFORMATION: inosine
<220> FEATURE:
<221> NAME/KEY: modified_base
<222> LOCATION: (22)..(23)
<223> OTHER INFORMATION: inosine
<220> FEATURE:
<221> NAME/KEY: modified_base
<222> LOCATION: (25)..(26)
<223> OTHER INFORMATION: inosine
<220> FEATURE:
<221> NAME/KEY: modified_base
<222> LOCATION: (28)..(31)
<223> OTHER INFORMATION: inosine

<400> SEQUENCE: 8
tttnnanccn tgnggnagna cnntnnannn ntatct                            36

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: inosine

```
<220> FEATURE:
<221> NAME/KEY: modified_base
<222> LOCATION: (5)..(6)
<223> OTHER INFORMATION: inosine
<220> FEATURE:
<221> NAME/KEY: modified_base
<222> LOCATION: (8)..(9)
<223> OTHER INFORMATION: inosine
<220> FEATURE:
<221> NAME/KEY: modified_base
<222> LOCATION: (12)..(12)
<223> OTHER INFORMATION: inosine
<220> FEATURE:
<221> NAME/KEY: modified_base
<222> LOCATION: (15)..(15)
<223> OTHER INFORMATION: inosine
<220> FEATURE:
<221> NAME/KEY: modified_base
<222> LOCATION: (18)..(19)
<223> OTHER INFORMATION: inosine
<220> FEATURE:
<221> NAME/KEY: modified_base
<222> LOCATION: (24)..(26)
<223> OTHER INFORMATION: inosine

<400> SEQUENCE: 9
ttnanngnna anacnggnnt attnnntgg                                          29

<210> SEQ ID NO 10
<211> LENGTH: 2167
<212> TYPE: DNA
<213> ORGANISM: Human T-cell leukemia virus

<400> SEQUENCE: 10 ggaagggaa cccctcctgt tggatctccc ttccacctca ggcactactg aggaaaaaaa        60
ctccttaagg ggggagatct aatctccccc catcccgatc aagacatctc gatactccca      120
ctcatccccc tgcggcagca acaacaacca attctagggg tccggatctc cgttatggga      180
caaacacctc agcctaccca agcgctactt gacacaggag ccgaccttac ggttataccc      240
cagacactcg tgcccgggcc ggtaaagctc cacgacaccc tgatcctagg cgccagtggg      300
caaaccaaca cccagttcaa actcctccaa accccctac acatattctt gcccttccga       360
aggtcccccg ttatcctttc ctcctgcctc ttagacaccc acaacaaatg gaccatcatt      420
ggaagggacg ccctacaaca atgccagggg cttctatacc ttccagacga ccccagcccc      480
caccaattgc tgccaatagc cacccaaac accataggcc tcgaacacct tccccacct       540 ccccaagtgg accaattttc tttaaacctg agcgcctcca ggcttaaat gacctggtct       600 ccaaggccct ggaggctggt cacattgaac catactcagg accaggcaat aaccccgtct      660
tccccgttaa aaaaccaaat ggtaaatgga ggttcattca tgacctaaga gccaccaatg      720
ccattactac cacccctcacc tctccttccc cagggccccc cgatctcact agcctaccga      780
cagccttacc ccacctacag accatagatc ttactgacgc cttttttcaa atcccctcc       840 ccaagcagta ccagccatac ttcgccttca ccattcccca gccatgtaac tatggccccg      900
ggaccagata tgcatggact gtccttccac aggggtttaa aaacagcccc accctcttcg      960
aacaacaatt agcagccgtc ctcaaccca tgaggaaaat gtttcccaca tcgaccattg     1020
tccaatacat ggatgacata cttttagcca gccccaccaa tgaggaatta caacaactct     1080
cccagctaac cctccaggca ctgaccacgc atggccttcc aatttcccag gaaaaaacac     1140
aacaaacccc aggccaaata cgcttcttag gacaggtcat ctcccctaat cacattacct     1200
atgagagtac ccctactatt cccataaaat cccaatggac actcactgaa ttacaagtta    1260
```

```
tcctaggaga gatccagtgg gtctctaaag gaacacccat ccttcgcaaa cacctacaat   1320
ccctatattc tgcccttcac gggtaccggg acccaagagc ttgtatcacc ctcacaccac   1380
aacaacttca tgcgttacat gccattcaac aagctctaca acataactgc cgtggccgcc   1440
tcaaccccgc cctacctctc cttggcctca tctcgttaag tacatctggt acaacatctg   1500
tcatctttca acccaagcaa aattggcccc tggcttggct ccacaccccc cacccctcga   1560
ccagtttatg tccttggggt cacctactgg cctgcaccat cttaactcta gacaaatata   1620
ccctacaaca ttatggccag ctctgccaat cttttccacca caacatgtca aagcaagccc   1680
tttgcgactt cctaaggaac tcccctcatc caagtgtcgg catcctcatt caccacatgg   1740
gtcgattcca taaccttggc agccaaccgt ctggtccgtg aagactctc ttacacctcc   1800 caacccttct ccaggaacca cgactcctca ggccaatttt caccctctcc ccgtcgtgc   1860 ttgacacggc ccctgccttt tttccgatg gctcccctca aaaggcagcg tacgttctct   1920
gggaccagac tatccttcaa caggacatca ctcccctgcc ttctcacgaa acaaattccg   1980
cacaaaaggg ggagctcctt gcacttatct gtggactacg tgctgccaag ccatggccct   2040
cccttaacat cttttagac tctaaatatt taatcaaata cctacattcc ctcgccattg   2100
gggccttcct cggcacttcc gcccatcaaa ccctccaggc ggccttacca ccctactgc   2160 agggcaa                                                              2167

<210> SEQ ID NO 11
<211> LENGTH: 2091
<212> TYPE: DNA
<213> ORGANISM: Human T-cell leukemia virus

<400> SEQUENCE: 11
tattagatct ccccgccgac atcccacacc caaaaaactc cataggggg gaggtttaac     60 ctccccccccc acattacagc aagtccttcc taaccaagac ccaacatcta ttctgccagt   120
tataccgtta gatcccgccc gtcggccgt aattaaagcc cagattgaca cccagaccag    180
ccacccaaag actatcgaag ctctactaga tacaggagca gacatgacag tccttccgat   240
agccttgttc tcaagtaata ctcccctcaa aaacacatcc gtgttagggg caggggggcca   300 aacccaagat cactttaagc tcacctcccct tcctgtgcta atacgcctcc ctttccggac   360
gacgcctatt gttttaacat cttgcctagt tgataccaaa acaactggg ccatcatagg    420 tcgtgatgcc ttacaacaat gccaaggcgt cctgtacctc cctgaggcaa aaaggccgcc   480
tgtaatcttg ccaatacagg cgccagctgt ccttgggcta gaacacctcc caaggccccc   540
cgaaatcagc cagttccctt taaaccagaa cgcctccagg ccttgcaaca cttggtccgg   600
aaggccctgg aggcaggcca tatcgaaccc tacaccgggc caggaaataa cccagtattc   660
ccagttaaaa aagccaatgg aacctggcga ttcatccacg acctgcgggc cactaactct    720
ctaaccatag atctctcatc atcttccccc gggcccctg acttgtccag cctgccaact    780
acactagccc acttacaaac tatagacctt aaagacgcct ttttccaaat cccctacct    840 aaacagttcc agcctacttt tgctttcact gtccacagc agtgtaacta cggccctggc    900
ccatatcctg cagcccattc ggcaagcctt ccccaatgc actattcttc agtacatgga    960
tgacattctc ctggcaagcc cctcccatgc ggacctgcaa ctactctcag aggccacaat   1020
ggcttcccta atctcccatg ggttgcctgt gtccgaaaac aaaacccagc aaaccctgg    1080 aacaattaag ttcctagggc aaataatttc acctaatcac ctcacttatg atgcagtccc   1140
caaggtacct atacggtccc gctgggcgct acctgaactt caagccctac ttggcgagat   1200
```

-continued

```
tcagtgggtc tccaaaggaa ctcctacctt acgccagccc cttcacagtc tctactgtgc    1260
cttacaaagg catactgatc cccgagacca aatatattta aatccttctc aagttcaatc    1320
attagtgcag ctgcggcagg ccctgtcaca gaactgccgc agtagactag tccaaaccct    1380
gcccctccta ggggctatta tgctgaccct cactggcacc accactgtgg tgttccagtc    1440
caagcagcag tggccacttg tctggctaca tgcccccta ccccacacta gccagtgccc    1500
ctgggggcag ctacttgcct cagctgtgtt attactcgac aaatacacct gcaatccta    1560 tggactactc tgccaaacca tacatcataa catctccacc caaaccttca accaattcat    1620
tcaaacatct gaccaccca gtgttcctat cttactccac cacagtcacc gattcaaaaa    1680
tttaggtgcc cagactggag aactttggaa cactttttctt aaaacaactg ccccattggc    1740
tcctgtgaaa gcccttatgc cagtgtttac tctttcccct gtgatcataa acaccgcccc    1800
ttgcctgttt tcagacggat ccacctccca ggcagcctat attctctggg acaagcatat    1860
attgtcacaa agatcattcc cccttccgcc accgcacaag tcggcccaac gggccgaact    1920
tctcggactt ttgcatggcc ctccagcgc ccgttcgtgg cgctgtctca acatatttct    1980
agactccaag tatctttatc attaccttcg gacccttgcc ctaggcacct tccaaggcag    2040
gtcctctcag gcccccttttc aggccctcct gccccgctta ctatcgcgta a            2091
```

<210> SEQ ID NO 12
<211> LENGTH: 2003
<212> TYPE: DNA
<213> ORGANISM: Human immunodeficiency virus

<400> SEQUENCE: 12

```
ttcagagcag accagagcca acagccccac cagaagagag cttcaggtct ggggtagaga      60
caacaactcc ccctcagaag caggagccga tagacaagga actgtatcct ttaacttccc     120
tcaggtcact ctttggcaac gaccctcgt cacaataaag ataggggggc aactaaagga     180
agctctatta gatacaggag cagatgatac agtattagaa gaaatgagtt tgccaggaag     240
atggaaacca aaaatgatag ggggaattgg aggtttatc aaagtaagac agtatgatca     300
gatactcata gaaatctgtg gacataaagc tataggtaca gtattagtag gacctacacc     360
tgtcaacata attggaagaa atctgttgac tcagattggt tgcactttaa attttcccat     420
tagccctatt gagactgtac cagtaaaatt aaagccagga atggatggcc caaaagttaa     480
acaatggcca ttgacagaag aaaaaataaa agcattagta gaaatttgta cagagatgga     540
aaaggaaggg aaaatttcaa aaattgggcc tgaaaatcca tacaatactc cagtatttgc     600
cataaagaaa aaagacagta ctaaatggag aaaattagta gatttcagag aacttaataa     660
gagaactcaa gacttctggg aagttcaatt aggaatacca catcccgcag gttaaaaaa     720 gaaaaaatca gtaacagtac tggatgtggg tgatgcatat ttttcagttc ccttagatga     780
agacttcagg aagtatactg catttaccat acctagtata aacaatgaga caccagggat     840
tagatatcag tacaatgtgc ttccacaggg atggaaagga tcaccagcaa tattccaaag     900
tagcatgaca aaaatcttag agccttttag aaaacaaaat ccagacatag ttatctatca     960
atacatggat gatttgtatg taggatctga cttagaaata gggcagcata gaacaaaaat    1020
agaggagctg agacaacatc tgttgaggtg gggacttacc acaccagaca aaaaacatca    1080
gaaagaacct ccattccttt ggatgggtta tgaactccat cctgataaat ggacagtaca    1140
gcctatagtg ctgccagaaa aagacagctg gactgtcaat gacatacaga agttagtggg    1200
```

```
gaaattgaat tgggcaagtc agatttaccc agggattaaa gtaaggcaat tatgtaaact    1260
ccttagagga accaaagcac taacagaagt aataccacta acagaagaag cagagctaga    1320
actggcagaa aacagagaga ttctaaaaga accagtacat ggagtgtatt atgacccatc    1380
aaaagactta atagcagaaa tacagaagca ggggcaaggc caatggacat atcaaattta    1440
tcaagagcca tttaaaaatc tgaaaacagg aaaatatgca agaatgaggg gtgcccacac    1500
taatgatgta aaacaattaa cagaggcagt gcaaaaaata accacagaaa gcatagtaat    1560
atggggaaag actcctaaat ttaaactgcc catacaaaag gaaacatggg aaacatggtg    1620
gacagagtat tggcaagcca cctggattcc tgagtgggag tttgttaata cccctccctt    1680
agtgaaatta tggtaccagt tagagaaaga acccatagta ggagcagaaa ccttctatgt    1740
agatggggca gctaacaggg agactaaatt aggaaaagca ggatatgtta ctaatagagg    1800
aagacaaaaa gttgtcaccc taactgacac aacaaatcag aagactgagt tacaagcaat    1860
ttatctagct ttgcaggatt cgggattaga agtaaacata gtaacagact cacaatatgc    1920
attaggaatc attcaagcac aaccagatca aagtgaatca gagttagtca atcaaataat    1980
agagcagtta ataaaaaagg aaa                                            2003
```